United States Patent [19]

Hendel

[11] Patent Number: 4,600,005
[45] Date of Patent: Jul. 15, 1986

[54] GUIDED OSTEOTOME FOR HARVESTING CRANIAL BONE GRAFT

[76] Inventor: Philip M. Hendel, 1722 Napoleon Ave., Apt. 1, New Orleans, La. 70115

[21] Appl. No.: 643,666
[22] Filed: Aug. 22, 1984
[51] Int. Cl.⁴ .............................................. A61B 17/16
[52] U.S. Cl. ........................................ 128/304; 30/167
[58] Field of Search .................. 128/304, 305; 30/168, 30/278, 167, 167.1, 167.2

[56] References Cited

U.S. PATENT DOCUMENTS

| | | | |
|---|---|---|---|
| 1,114,903 | 10/1914 | Moore | 30/168 |
| 1,401,635 | 12/1921 | Olcott | 30/278 |
| 1,554,307 | 9/1925 | Tarantino | 30/168 |
| 2,757,452 | 8/1956 | Barnes | 30/168 |
| 3,610,246 | 10/1971 | Salmon | 128/305 |
| 3,673,686 | 7/1972 | Benedict, Jr. | 30/168 |
| 3,834,393 | 9/1974 | Goggins | 128/305 |
| 4,221,222 | 9/1980 | Detsch | 128/304 |
| 4,239,045 | 12/1980 | Schlein | 128/305 |

FOREIGN PATENT DOCUMENTS

| | | | |
|---|---|---|---|
| 0902734 | 2/1982 | U.S.S.R. | 128/305 |
| 1107855 | 8/1984 | U.S.S.R. | 128/305 |

Primary Examiner—Robert Peshock
Assistant Examiner—David I. Tarnoff
Attorney, Agent, or Firm—Pravel, Gambrell, Hewitt & Kimball

[57] ABSTRACT

A guided osteotome for use in the harvesting of bone graft material for craniofacial plastic surgery includes an instrument body having a blade on the instrument body with a cutting edge for cutting through a layer of selected bone tissue suitable for grafting. The blade includes a flattened portion adjacent the cutting edge and lateral guides positioned on the blade on opposite edge portions of the cutting edge. The guides define the depth of cut of the cutting edge and include one or more bearing surfaces which track upon the surface of a patient's skull during the bone graft harvesting operation.

14 Claims, 10 Drawing Figures

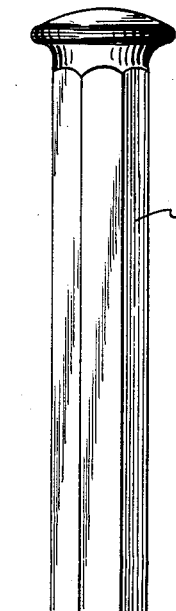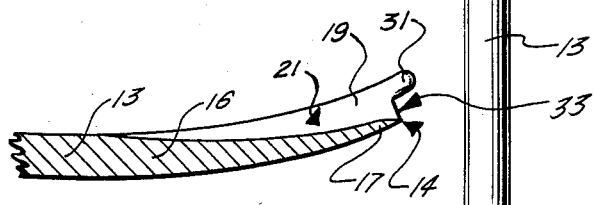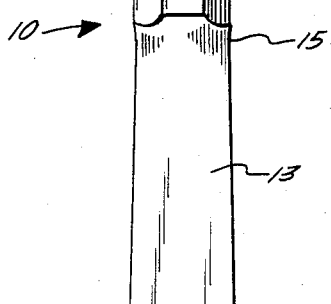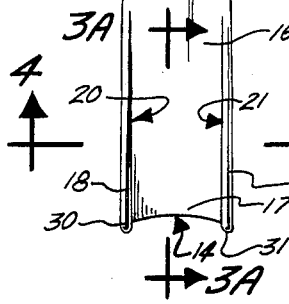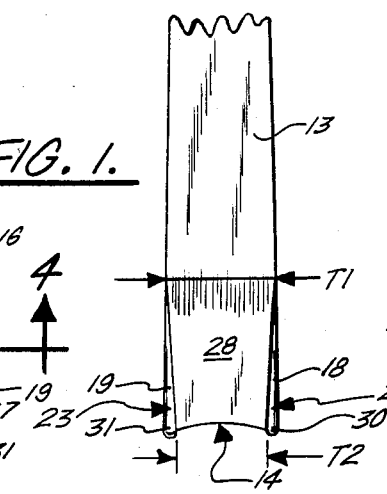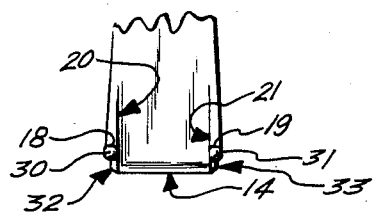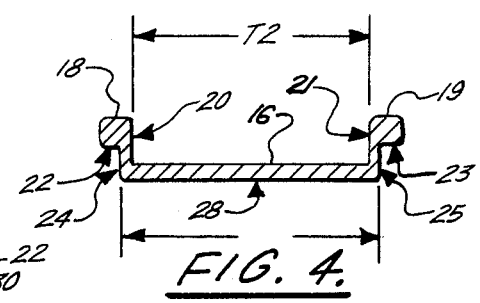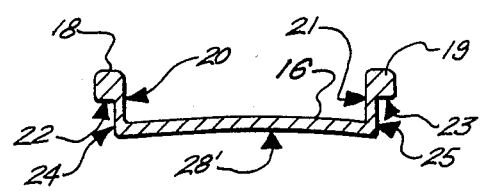

GUIDED OSTEOTOME FOR HARVESTING CRANIAL BONE GRAFT

BACKGROUND OF THE PRESENT INVENTION

1. Technical Field

The present invention relates to surgical instruments useful in a sub-specialty of the field of plastic surgery referred to as craniofacial surgery.

2. General Background

Craniofacial surgery deals with surgical reconstruction of the skeleton of the face and cranium and the reconstruction of other like bony structures. There are certain advantages in the use of a cranial bone graft for facial reconstruction. The donar area is substantially painless as compared to sites such as the rib or the hip. The quality of bone graft material is superior for use in reconstruction, as it is more readily incorporated into the recipient bed and there is less resorption during healing. The harvesting of bone graft material from this area usually produces less surgical dissection overall, as the same exposure can be used for both the reconstruction and for the harvesting of the bone graft. This latter advantage also results in a saving of operating time.

Previous techniques have been described for the harvesting of bone grafts from the cranium for use in craniofacial surgical reconstruction. These techniques have included inter alia, using a neurosurgical drilling device called a "cranial perforator" to harvest "bone dust" by drilling through the outer two layers of the skull at multiple sites. Some techniques have used a standard osteotome (basically, a chisel) having either a straight or curved blade with a free hand technique to tangentially chip off sections of the outer layer of the cranium. Neurosurgical devices have been used to cut out a full thickness piece of skull. This entire section of the cranium is then taken to a separate working area in the operating room where it is split between the inner and outer tables using sharp chisels. Either the inner or the outer layer can then be used for the surgical reconstruction. The remaining layer is returned to the donar site to fill in the hole left in the cranium.

Problems exist with prior art devices and methods of harvesting bone graft material from the cranium. Cranial perforators only harvest a bone powder material. This type of powder material is difficult to use because it is not rigid. It can only be used as a "packing" substance and cannot be used to make solid forms. While the method of using a free chisel to tangentially chip off the outer layer provides solid pieces of bone suitable for a wider range of reconstructive procedures, this method suffers from two problems. Firstly, the surgeon has no way of visualizing the depth of the cut he is making, thus the procedure is "blind." In addition, there is a dangerous possibility of the blade penetrating through the cranium and into the brain tissue below. Due to such a risk, this "chisel" technique has not found wide acceptance. The third method of splitting a full thickness plate of cranium harvested by neurosurgical techniques, has the advantage of providing large pieces of solid bone graft material for the surgical reconstruction. It suffers in that an extensive neurosurgical procedure is required to harvest the original full thickness plate of cranium. Besides being time-consuming it is also not free of risk. Further, this procedure usually requires a second surgical team, adding complexity and expense.

General Discussion of the Present Invention

The present invention solves these prior art problems and shortcomings in a straightforward, simple yet effective manner by providing a guided osteotome. The guided osteotome is an instrument that harvests bone graft material in rigid pieces of pre-determined, generally uniform thickness. The device includes a blade that is preferably longitudinally curved away from the curve of the surface of the cranium to impede the blade's tendency to "plunge" as it advances. The guided osteotome of the present invention has laterally extending guides having bearing surfaces which "track" the surface of the cranium during harvesting, thus physically limiting the depth of cut and thereby preventing the cutting element from plunging deeper than a predetermined known depth which also desirably defines the thickness of a layer of bone graft material harvested. The guides also can project forward of the cutting edge allowing the surgeon to visually monitor linear progression of the cutting edge along the skull during cutting. The device can be used without the need of supportive neurosurgery techniques that accompany exposure of the underlying brain.

The present invention thus provides a guided osteotome that is both safer and easier to use for harvesting cranial bone grafts. The apparatus features a shaft with a handle supporting a longitudinal curved blade having a longitudinal curve opposite the curve of the outer surface of the cranium. The blade thus lessens the tendency for the blade cutting edge to plunge to a deeper depth as it advances.

The guided osteotome of the present invention is used in the harvesting of bone graft for craniofacial plastic surgery. The apparatus includes an elongated instrument body having a blade which includes a transverse cutting edge for cutting through a layer of selected cranial bone tissue suitable for use as a graft. The blade includes a flattened portion adjacent the transverse cutting edge. One or more guides are positioned on the blade, preferably on opposite edge portions thereof for defining the depth of cut. The guide includes one or more bearing surfaces which track upon the surface of a patient's skull during the bone graft harvesting operation. In the preferred embodiment, two spaced apart guides are disposed generally on opposite edge portions of the blade. In the preferred embodiment, the guides include a pair of spaced apart guides, each of which has a first bearing surface generally parallel to the cutting edge which is that surface that rides upon the surface of the patient's skull during the bone graft harvesting. A second surface extends angularly (preferably at right angles) between the first bearing surface and the transverse cutting edge, thereby forming a connection between the first bearing surface and the flattened portion of the blade. In the preferred embodiment, the guides are in the form of one or more projections which extend forwardly of the transverse cutting edge. Each of the forwardly extending projections is rounded in cross-section in the preferred embodiment. The transverse cutting edge can be curved, corresponding to the curvature of the patient's skull. This latter embodiment is especially useful in making wider cuts to harvest wider sections of graft material.

It has been found that for the human skull an exemplary radius of seven (7.0) centimeters over 22 degrees for the cutting edge is useful. The blade can then be tapered straight over the next 22 degrees. Because the surface of the human skull is curved in two directions, it has also been found that if the blade is wider than one (1.0) centimeter, precautions must also be taken to stop the center portion of the blade from penetrating the skull "inner table." It is necessary in the wider blades to give the transverse aspect of the cutting edge a curvature to match that of the cranium to avoid this problem. The most efficacious transverse curvature is radius 7.0 centimeters. This can either be accomplished by curving the bottom of the blade itself or by sharpening the end as a curve so that the center of the blade is withdrawn up the curve of the shaft and is functionally higher than the sides during the cutting process.

To give control to the depth of the cut and in particular to prevent application through the cranium, the sides of the blades are also provided with the aforementioned guides. These guides act like small skids that ride along the surface of the outer table of the cranium while the blade cuts below. These guides are manufactured at standard preset depths, for example, one (1.0), two (2.0) or three (3.0) millimeters, giving the surgeon several options as to the thickness of the bone graft material he can harvest.

Pre-operatively the surgeon will check the thickness of the skull by X-ray before deciding upon a thickness for the graft material. Not only do the guides act to physically impede plunging of the blade into the skull, but they are a fixed point of reference in relation to the cutting edge. The surgeon can thus visually monitor these two points as the cut progresses longitudinally so that the cutting action is not done blindly. The guides include projections which can be designed to project forward beyond the front of the cutting edge a predicted distance so that, for example, the angle between the line of the longitudinal end tangent of the blade and the line between the tip of the guides and the tip of the blade is forty-five degrees (45%).

The technique of use of the present invention follows: Following an X-ray to estimate the thickness of the skull outer table, two parallel cuts are made along the proposed path of the osteotome through the outer table of the cranium. This is done using any type of cranial saw. The cuts are parallel and spaced apart a distance equal to the width of the osteotome to be used. The depth of the saw cuts is through the outer table only. The surgeon can visually judge this depth because the diploe is a different color then the outer table bone. Once this has been done, a cross cut is made at right angles, or ninety degrees (90%) to the longitudinal cuts and at one end thereof (FIG. 5). The right angle cut is made to the same depth and joins the two parallel cuts. Once the outer table has been prepared, the cutting edge of the osteotome is placed in the cross cut and a mallet or hammer is used to drive the osteotome along the path of the two parallel side cuts. The two parallel cuts prevent the osteotome from skidding laterally of the projected path. The two guides slide along the skull surface preventing the blade from plunging into the skull beyond the predetermined depth. In addition, the surgeon visually monitors the progress of the transverse blade cutting edge. Once the blade has been passed and the bone graft taken, bone wax is applied to the raw surface of bone (i.e., the upper surface of the inner table) to control bleeding. No further reconstruction of the donar defect is necessary.

The instrument body could be a frame supporting a power driven cutting element having a powered blade such as a reciprocating or band saw blade, for example. The guides could be thus supported by the frame so that the cutter would likewise harvest bone graft material of a uniform defined depth. A reciprocating blade would oscillate while travelling along the path of two parallel cuts made in the outer table of the skull and spaced apart a distance equal to or greater than the excusion of oscillation.

BRIEF DESCRIPTION OF THE DRAWINGS

For a further understanding of the nature and objects of the present invention, reference should be had to the following detailed description, taken in conjunction with the accompanying drawings in which the parts are given like reference numerals and wherein:

FIG. 1 is a top view of the preferred embodiment of the apparatus of the present invention;

FIG. 2 is a fragmentary side of the preferred embodiment of the apparatus of the present invention illustrating the blade portion thereof;

FIG. 3A is a sectional view taken along lines 3A—3A of FIG. 1;

FIG. 3B is a fragmentary bottom view of the preferred embodiment of the apparatus of the present invention illustrating the blade and cutting edge portions thereof;

FIG. 4 is a sectional view taken along lines 4—4 of FIG. 1;

FIG. 5 is sectional view of the preferred embodiment of the apparatus of the present invention illustrating an alternate embodiment thereof;

FIG. 6 is a fragmentary front perspective of the preferred embodiment of the apparatus of the present invention;

DETAILED DESCRIPTION OF THE PREFERRED EMBODIMENT

Figure 8:
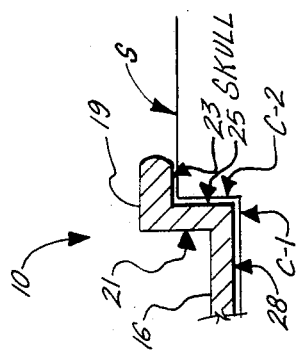
FIG. 8 is a schematic view of the preferred embodiment of the apparatus of the present invention showing the relationship between the cutting blade, guides, and the skull of the patient during the bone harvesting operation.

FIG. 1 shows generally the preferred embodiment of the apparatus of the present invention designated generally by the numeral 10. Guided osteotome 10 includes a blade body 15 which is elongated having at one end portion a gripping surface 12 defining a handle and at the other end portion a blade 13 which is joined to the handle and extends therefrom. The handle end portion can provide an impact receptive head 11 so that it can be hammered with a mallet or the like during operation.

The blade 13 includes a generally flattened distal end portion 16 which gradually tapers to a narrowed section 17 which terminates at cutting edge 14. The blade flattened distal end portion 16 terminates laterally at a pair of guides 18, 19. These guides, as will be described more fully hereinafter, define the depth of cut of the cutting edge 14 as the surgeon forces the cutting edge along the surface of the patient's skull during a bone graft harvesting operation.

Guides 18, 19 each provide respective interior vertical surfaces 20, 21 and exterior vertical surfaces 24, 25. The surfaces 20, 24 of guide 18 can forwardly taper joining at edge 32. Likewise, guide 19 forwardly tapers until surfaces 21, 25 join at edge 33 (see FIGS. 4 and 6). Each guide 18, 19 also provides a lowermost flat surface 22, 23 respectively. These flat surfaces 22, 23 define bearing surfaces which track upon the surface of the cranium during the bone graft harvesting operation.

The sectional views of FIGS. 4 and 5 best show the bearing surfaces 22, 23. The bearing surfaces 22, 23 can also be seen in the bottom view of FIG. 3B. FIGS. 4 and 5 show different embodiments of the flat 16 portion of the cutting blade. In FIG. 4, the cutting blade 16 is generally flat providing a flattened lower surface 28. In FIG. 5, another embodiment shows a curved cutting blade which would have a correspondingly curved cutting edge. In FIG. 5, the lower surface 28 prime of the flattened portion 16 of the cutting blade is curved. This curvature would preferably be a curvature which corresponds to the curvature of the human skull. An exemplary radius of curvature for example, would be seven centimeters (7.0). Otherwise, the guides 18, 19 would be correspondingly constructed to the guides as shown in the embodiment of FIG. 4.

Figure 7:
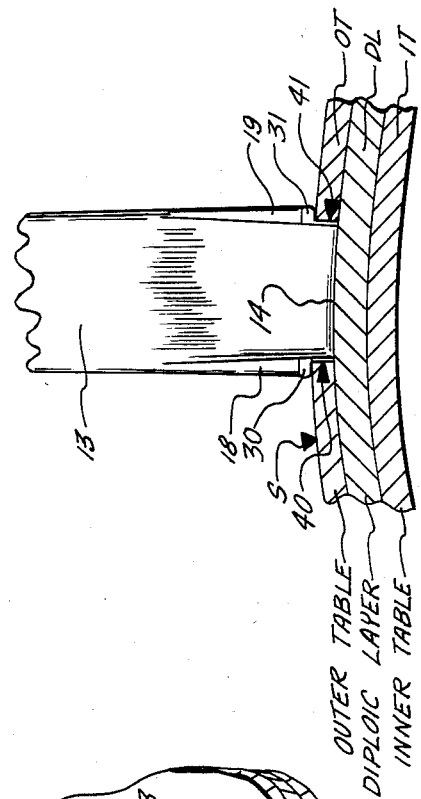
FIG. 7 is a schematic view of the preferred embodiment of the apparatus of the present invention shown harvesting a layer of the cranial outer table.
Figure 9:
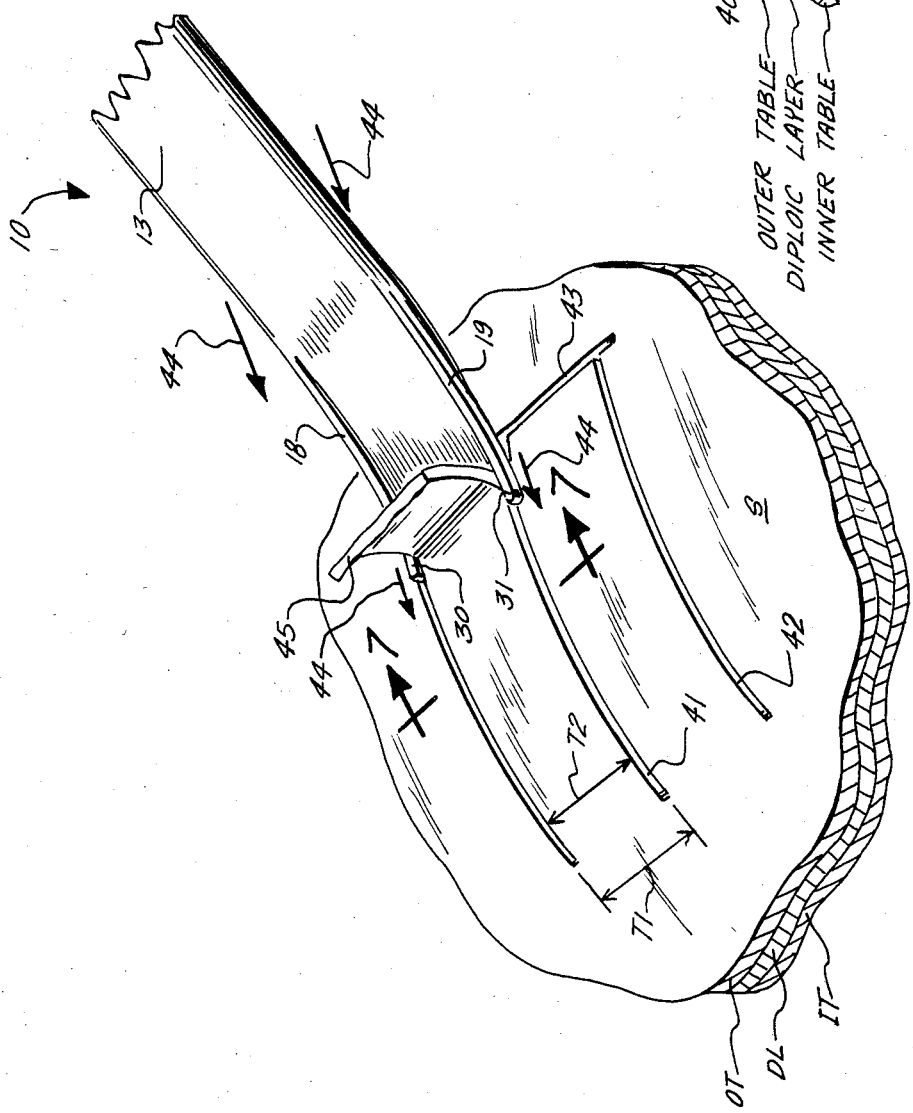
FIG. 9 is a perspective view of the preferred embodiment of the apparatus of the present invention illustrating its use to remove a layer of bone graft material from the cranium of the patient.

FIGS. 7–9 illustrate the preferred embodiment of the apparatus of the present invention during operation. In FIGS. 7 and 9, there is schematically illustrated a portion of the skull "S" of a patient including multiple layers which are known as the outer table (OT), diploic layer (DL) and inner table (IT). The surgeon would first make a plurality of parallel longitudinally running cuts 40–42. The surgeon would then make a transverse cut 43 at substantially right angles to the cuts 40–42 and connecting one common end portion of the cuts 40–42. This arrangement can be seen best in FIG. 9. The cuts would all be of a depth equal to the depth of the outer table which is the portion of cranial tissue to be grafted. The transverse saw cut 43 defines a point of beginning for guided osteotome 10. The arrows 44 in FIG. 9 illustrate the longitudinal direction in which osteotome 10 proceeds. The forward projections 30, 31 of each respective guide 18, 19 rests upon the surface of the patient's skull S as best seen in FIG. 7. Thus, the surgeon can visually inspect the projections 30, 31 as the guided osteotome 10 moves in the direction of arrows 44.

FIGS. 7 and 8 schematically illustrate the position of cutting edge 14 and of blade 16 during the bone graft harvesting operation. FIG. 7 shows the blade 14 extending downwardly through the outer table and laterally until it reaches the saw cuts 40, 41. Saw cuts 40, 41 are dimensioned apart so that the harvested strip of graft material will fit between the vertical surfaces 20, 21. Thus, the lateral dimension of bone graft material harvested would be equal to or slightly less than the dimension T2. The dimension T2 would be the lateral dimension T2 (i.e., lateral dimension of the grafted material) plus the additional lateral dimension added by the thickness of the saw which forms the cut 40, 41. Thus, the dimension T2 would be large enough to accommodate the blade 16 as well as the lower portion of guides 18, 19 between surfaces 24, 25. FIG. 8 schematically illustrates the position of guided osteotome 10 during the cut. In FIG. 8, there is shown one guide 18 of the osteotome 10. The guide 19 includes a lower bearing surface 23 portion which abuts and tracks upon the surface S of the skull during operation. Exterior vertical surface 25 of guide 19 is positioned interiorly with the vertical cut C2 which is formed by the saw (not shown) which makes cuts 40–42. The cut C1 as shown in FIG. 8 is that surface formed by the cutting edge 14 of the flattened end portion 17 of the blade. In the preferred embodiment, notice that the surface 23 of guided osteotome 19 which forms the bearing surface portion thereof is generally parallel to the surface 28 which is the underside surface of the blade flattened end portion 16.

The guided osteotome as shown in the preferred embodiment could be made of any suitable surgical instrument material such as stainless steel, for example. In the embodiment shown, the overall length of the device would be approximately 20 centimeters while the overall lateral dimension T1 at the cutting edge 14 would be, for example, 20 millimeters and the dimension T2 between guides 18, 19 would be, for example, 17 millimeters.

Because many varying and different embodiments may be made within the scope of the inventive concept herein taught, and because many modifications may be made in the embodiment of the law, it is to be understood that the details herein are to be interpreted as illustrative and not in a limiting sense.

What is claimed as invention is:

1. A guided osteotome for use in the harvesting of cranial bone graft material for use in craniofacial plastic surgery, comprising:
   a. an instrument body;
   b. blade means on the instrument body including a cutting edge for cutting through layer of selected bone tissue suitable for grafing;
   c. the blade means including a generally flattened portion adjacent the cutting edge;
   d. guide means for defining the depth of a cut of the cutting edge and including a pair of spaced apart guides, each respectively having a bearing surface which tracks upon the skull during a bone graft harvesting operation when the cutting edge is generally parallel to the surface of the patient's skull, and a transverse surface extends angularly between each bearing surface and the cutting edge; and
   e. the blade and guide means being an integral unit which defines a recess through which harvested graft material can pass.

2. The guided osteotome of claim 1 wherein there are two spaced apart guide means disposed generally on opposite edge portions of the blade means.

3. A guided osteotome for use in harvesting cranial bone graft material to be used in craniofacial plastic surgery, comprising:
   a. an instrument body;
   b. blade means carried by the instrument body and including a laterally extending cutting edge;
   c. a pair of guide means carried by the instrument body and including surface means, positioned laterally on the side of the blade means, which tract upon the patient's cranium for defining the depth of cut of the blade means so that the blade means does not completely penetrate the cranium and contact underlying brain tissue; and
   d. the guide means and blade means being an integral unit which forms a recess through which harvested bone graft material can pass.

4. The guided osteotome of claim 1 wherein the first surface projects forwardly of the cutting edge.

5. The guided osteotome of claim 1 wherein the guide means includes one or more projections which extend forwardly of the cutting edge.

6. The guided osteotome of claim 5 wherein the projections are rounded in cross-section.

7. The guided osteotome of claim 1 wherein the blade means includes a curved cutting edge that generally corresponds to the curvature of the patient's skull.

8. The guided osteotome of claim 7 wherein the blade means has a radius of curvature of seven (7) centimeters.

9. The guided osteotome of claim 1 wherein the guide means includes a pair of skids which are positioned on each side of the blade cutting edge and connected thereto respectively by a pair of generally vertical webs which each extend respectively between the blade means at the cutting edge and the skids.

10. A guided osteotome for harvesting uniform layers of bone tissue from the skull of a patient, comprising:
    a. a handle handing an impact receiptive head that can be hammered;
    b. a shaft extending from the handle;
    c. a blade projecting from the shaft and including at its free end, a cutting edge;
    d. a pair of spaced apart bearing surface means positioned at the side portions of the blade which register upon the skull of the patient during the harvesting of bone graft material from the patient's skull for defining a preselected uniform depth of cut for the blade as the blade is forced along and through the outer table of the skull; and
    e. a pair of generally vertical web means extending respectively between the bearing surface means and the blade and being an integral unit therewith, defining a recess with the blade through which harvested graft material can pass.

11. The guided osteotome of claim 10 wherein the blade includes a generally flat distal end portion having a cutting edge which traverses a cut projection and the bearing surface includes one or more generally flat surfaced guides having one or more surfaces which occupy a plane that is generally parallel to a cut projection traversed by the blade distal end.

12. The guided osteotome of claim 10 wherein the cutting edge has a lateral curvature that generally corresponds to the skull curvature.

13. The guided osteotome of claim 12 wherein the bearing surface means includes a pair of guides that are joined to the blade.

14. The guided osteotome of claim 13 wherein each guide includes interior and exterior vertical surfaces which intersect respectively the upper and lower surfaces of the blade.

* * * * *